United States Patent [19]
Emmons

[11] 3,989,752
[45] Nov. 2, 1976

[54] NOVEL DIFUNCTIONAL COMPOUNDS AS LATENT DIISOCYANATES

[75] Inventor: William D. Emmons, Huntingdon Valley, Pa.

[73] Assignee: Rohm and Haas Company, Philadelphia, Pa.

[22] Filed: Jan. 5, 1970

[21] Appl. No.: 832

Related U.S. Application Data

[63] Continuation-in-part of Ser. No. 563,095, July 6, 1966, abandoned.

[52] U.S. Cl. .................... 260/561 H; 260/77.5 AP; 260/453 P; 8/115.6; 8/128 R
[51] Int. Cl.² ...................................... C07C 109/087
[58] Field of Search ............................... 260/561 H

[56] References Cited
UNITED STATES PATENTS

| | | | |
|---|---|---|---|
| 3,450,673 | 6/1969 | McKillip | 260/75 |
| 3,706,797 | 12/1972 | McKillip et al. | 260/561 H X |

*Primary Examiner*—Ethel G. Love

[57] ABSTRACT

N,N'-bis(trialkylamino)alkanediimides are useful as intermediates for forming latent isocyanates which in turn are useful for curing polymers containing active hydrogen, and as reactants in the production of polyurethane resins. The difunctional N,N'-bis(trialkylamino)alkanediimides are prepared by reacting a dicarboxylic acid dihydrazide with an alkyl halide to quaternize the dihydrazide and then neutralizing the resulting salt with an appropriate base in either aqueous or alcohol medium.

1 Claim, No Drawings

NOVEL DIFUNCTIONAL COMPOUNDS AS LATENT DIISOCYANATES

CROSS-REFERENCE TO RELATED APPLICATION

This application is a continuation-in-part of my co-pending U.S. application Ser. No. 563,095, filed on July 6, 1966, now abandoned.

This invention relates to new compounds and to a method for preparing them. More particularly it relates to N,N'-bis-(trialkylamino)alkanediimides, to methods of preparing isocyanates from said compounds, and to the use of said compounds as latent isocyanates in curing polymers containing active hydrogen.

The reactivity of the isocyanate radical with compounds containing active hydrogen is known. This high degree of reactivity is used in a host of reactions to produce valuable polymers and compounds. Thus polyisocyanates are reacted with hydroxyl-terminated polyesters and/or polyethers to produce useful polyurethane resins. Other polyurethanes are produced by the reaction of polyisocyanates with aminoalcohols, with esteramides, with polysulfide polymers, etc. In addition to such reactions which may be used to produce chain-extended polymers, polyisocyanates are also added to polymeric compositions containing active hydrogen to cross-link the polymeric chains.

While the high degree of reactivity of the isocyanate radical makes possible this versatility, it is also the source of continuing difficulties in adapting isocyanate compounds to such uses. This difficulty arises from the fact that the high degree of reactivity between the isocyanate radical and molecules containing active hydrogen causes reactions to occur prematurely and further makes the reaction difficult to control. To solve such difficulties "blocked" isocyanates have been developed. In a blocked isocyanate a reversible reaction is used to form an adduct which can be decomposed by heating. A host of reactions have been utilized for this purpose. A comprehensive list of compounds used in forming blocked isocyanates is given in U.S. Pat. No. 2,801,990 to Seeger et al. Generally, the decomposition products of such prior art materials (as, for example, a phenol) pose problems by their presence and in any event are difficult to remove. Moreover, the adducts also have in common a general scheme of preparation which involves first, synthesizing the isocyanate and then forming the adduct of the isocyanate which serves as the "blocked" isocyanate.

The broad object of this inventon is to provide a new class of chemical compounds which are difunctional N-trialkylamine alkylimides.

It is a further object of the invention to provide a novel process for synthesizing difunctional isocyanates under carefully controlled conditions.

Again, it is an object of the invention to provide a diisocyanate precursor which itself serves as a blocked or latent diisocyanate.

Yet again, an object of the invention is to provide a novel, latent diisocyanate which has excellent stability.

Another object of the invention is to provide a composition comprising a latent diisocyanate and one or more polymers containing active hydrogen in the polymer chain which compositions have excellent stability and pot life while being easily cured to a thermosetting condition at moderate temperatures.

These and other objects of the invention will become apparent from the following description and examples of the invention.

The above objects of the invention are attained by reacting a dicarboxylic acid dihydrazide with an alkyl halide to quaternize the dihydrazide and then neutralizing the resulting salt with an appropriate base in either aqueous or alcoholic medium. The difunctional N,N'-bis(trialkylamino)alkanediimide so obtained (hereinafter termed an "N—N ylid") is easily converted to the diisocyanate by heating. This series of reactions may be illustrated as follows:

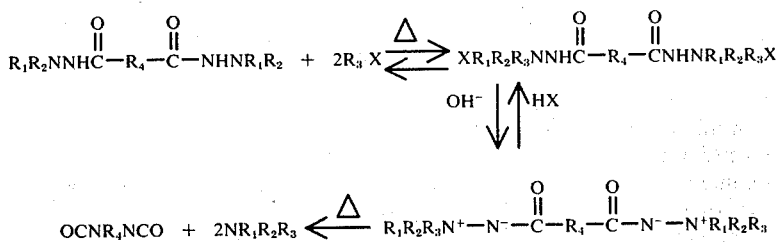

wherein $R_1$, $R_2$ and $R_3$ are lower alkyl radicals which jointly form a volatile tertiary amine and may be the same or different (i.e., volatile at the temperature of decomposition of the N—N ylid), $R_4$ is an aliphatic hydrocarbon radical or a cycloaliphatic hydrocarbon radical having from 1 to 24 carbon atoms and may be straight chain or branched, saturated or unsaturated, and X is a halogen having a molecular weight of at least 35. By reason of cost and ease of volatilization it is preferred that $R_1$ and $R_2$ be methyl and that $R_3$ be a $C_1$ to $C_5$ alkyl group. Where $R_1$, $R_2$ and $R_3$ are all the same, they should each have no more than three carbon atoms.

The dicarboxylic acid dihydrazides are known materials and may be produced by a variety of processes. Thus, they may be prepared by reacting the dicarboxylic acid dichloride with an unsymmetrical dialkyl hydrazine, preferably unsymmetrical dimethyl hydrazine. The quaternary salts produced by reacting the dicarboxylic acid dihydrazides with the alkyl halides as described are themselves thermally labile. Accordingly, they should be used in aqueous systems only at a pH of 9 or higher so as to allow complete conversion to the corresponding N—N ylid.

The N—N ylids of the invention decompose at moderate temperatures, decomposition generally being obtained at temperatures as low as about 140° C. The precise temperature for the dissociation reaction will vary somewhat with the nature of the N—N ylid. At lower temperatures (and in particular under normal storage conditions), the N—N ylids are highly stable even in the presence of active hydrogen-containing compounds.

It should be noted that the reaction by which the N—N ylid decomposes or rearranges to the corresponding diisocyanate offers certain analogies to the well-known Curtius reaction. However, the precise mechanism of the decomposition or rearrangement reaction used in the instant process is not known.

In fabricating articles using a polymeric material it is necessary to be able to subject it to processing conditions, often for extended periods, after the addition of the chemical needed to cause the transformation of the polymeric material from its uncured to its cured state. Thus, for example, after addition of the curing agent and other chemicals, it is necessary to subject the polymeric mixture to a mixing or blending operation, optionally followed by a forming operation as sheeting, spinning or coating, before the material is cured. These operations often involve some heating. If the curing agents react immediately upon addition or upon mild heating, it is difficlt to obtain a uniform cure or to carry out the manipulative steps necessary for the processing of the polymeric material. It is often desired to prepare blends of the curing agent and other chemicals with the polymeric material in sufficient quantity to satisfy the needs of a plant for a shift, a day or a workweek. If such a combination lacks stability, then new batches must be mixed at frequent intervals with corresponding less in efficiency and increased difficulties in scheduling manufacturing operations.

The use of the diisocyanate precursors of the invention minimizes such difficulties. The N—N ylids of the invention may be uniformly dispersed in polymers containing at least one active hydrogen per polymer chain (as copolymers of at least one mono- or di-unsaturated compound with at least one monomer such as acrylic acid, acrylamide, itaconic acid, allyl alcohol, hydroxypropyl methacrylate, hydroxyethyl methacrylate, hydroxyl or carboxyl-terminated polyesters or polyethers, cellulose esters or ethers containing free hydroxyl groups, diisocyanate-modified polyesters or polyethers as disclosed in U.S. Pat. No. 2,801,990, etc.) to produce stable compositions which are stable even when subjected to mild heating, as temperatures below 100° C. Such compositions have excellent pot life. When the material has been formulated and/or fabricated into its desired form, reaction between the isocyanate groups and the active hydrogen in the polymer chain is effected by moderate heating, i.e., to a temperature of 140° C. or above which causes the N—N ylid to rearrange or decompose generating the diisocyanate in situ. The —NCO groups so formed then react with the active hydrogen groups available to cure, cross-link or extend the polymer chain of the product. The by-product of the rearrangement, the tertiary amine, being volatile is completely and easily removed from the reaction medium. Moreover, being free of active hydrogen, the tertiary amine does not enter into any side reactions to form undesired by-products. Further, to the extent that it dissolves in the reaction medium prior to volatilization, the tertiary amine catalyzes the reaction between the isocyanate groups and the active hydrogen groups.

Moreover, utilizing N—N ylids as isocyanate precursors makes possible the synthesis of a number of isocyanates which are difficult to obtain by conventional processes and eliminates the necessity for handling phosgene. The high degree of stability of the N—N ylids makes it possible to use unsaturated N—N ylids in preparing copolymers from monomers containing active hydrogen groups and then generating the isocyanate group when desired, either to promote crosslinking of the polymer and/or to promote bonding to a substrate possessing active hydrogen-containing groups as cotton and wool textiles, etc.

The following examples illustrate the invention. All parts are by weight unless otherwise stated.

EXAMPLE 1 bis(N,N-dimethyl hydrazide) of sebacic acid

Into a 5 l., three-necked flask equipped with a mechanical stirrer, a reflux condenser surmounted with a drying tube, a a pressure-equalizing addition funnel is placed 121 g. (2.0 moles) of unsym.-dimethylhydrazine, 204 g. (2.0 moles) of triethylamine, and 3 l. of dry benzene. Sebacyl chloride, 239.1 g. (1.0 mole) is added to the stirred solution over a period of 15 minutes. The precipitation of a white solid begins immediately upon addition of the acid chloride. After the addition the stirred reaction mixture is refluxed for approximately one hour. The mixture is allowed to cool slightly then filtered with suction through a heated funnel. The filtrate is cooled to about 10° and the resulting white solid removed by suction filtration. The solid (175.3 g.) is dried under reduced pressure, m.p., 128°–132°. An additional 45–46 g. of the product (m.p., 122°–126°) is obtained by extraction of the solid originally obtained from the reaction mixture with the heated filtrate from the first crop. An overall crude yield of 77% (based on sebacyl chloride) is obtained.

Recrystallization of the first crop (175.3 g.) from acetone (5.2 l.) gives 134 g. of bis(N,N-dimethyl hydrazide) of sebacic acid, m.p. 136°–137°.

Anal., Calc'd for $C_{14}H_{30}N_4O_2$: C, 58.71%; H, 10.56%; N, 19.56%. Found: C, 58.88%; H, 10.50%; N, 19.45%.

Sebacyl bis(N,N,N-Trimethylhydrazonium chloride)

Into a 1 l. autoclave equipped with a mechanical stirrer is charged 71.5 g. (0.25 mole) of bis(N,N-dimethyl hydrazide) of sebacic acid, 400 ml. of benzene and 72 g. (1.43 moles) of methyl chloride. The contents are heated with stirring at 100° C for 10 hrs., then allowed to cool to room temperature. The resulting slurry is filtered with suction and the collected, white solid is dried under reduced pressure yielding 93.0 g. (96% yield), m.p., 212°–214° C (decomp.). Recrystallization from methanol (600 ml.) followed by drying under reduced pressure at mild temperatures affords 75.0 g. (77.5% yield) of sebacyl bis(N,N,N-trimethylhydrazonium chloride), a white crystalline solid, m.p. 220°–222° (decomp.). Further drying under vacuum for 2 hrs. at 78° raises the melting point to 222°–223° (decomp.).

Anal., Calc'd for $C_{16}H_{36}N_4O_2Cl$: C, 49.61%; H, 9.37%; N, 14.46%; Cl, 18.30%. Found: C, 49.69%; H, 9.41%; N, 14.29%; Cl(total), 18.26%.

N,N'-bis(trimethylamino) sebacyldiimide

To a stirred mixture of 77.5 g. (0.20 mole) of sebacyl bis-(N,N,N-trimethylhydrazonium chloride in 400 ml. of anhydrous methanol is added 86.5 g. (0.40 mole) of sodium methoxide (25% in methanol). The mixture is stirred for one hour at ambient temperatures then stripped under reduced pressure. The resulting white solid is extracted with 350 ml. of boiling methylene chloride and the remaining solid is washed with additional methylene chloride. The combined extracts are stripped under reduced pressure yielding 61.4 g. of an off-white solid, m.p. 136°–140°. Recrystallization from acetone (700–800 ml.) followed by vacuum drying at 56° for 1–2 hrs. affords 47.1 g. (75% yield) of N,N'-bis(trimethylamino) sebacyldiimide, m.p. 143°–5° C.

Anal., Calc'd for $C_{16}H_{34}N_4O_2$: C, 61.11%; H, 10.90%; N, 17.82%. Found: C, 60.55%; H, 11.02%; N, 17.38%.

EXAMPLE 2

Into a 50 ml. round bottom flask equipped with a conventional Claisen still-head, condenser and receiver is placed 15.7 g. (50 mmoles) of N,N'-bis(trimethylamino) sebacyldiimide. The solid is heated under vacuum (0.5 mm Hg.) by means of an oil bath. When the bath temperature reaches 160° all of the solid has melted; at 165°–170° decomposition becomes apparent as evidenced by gas evolution (trimethylamine). As the temperature is raised to 205° gas evolution increases then subsides; distillation finally occurs affording 6.3 g. (64.4% yield) of a colorless liquid. Redistillation of this material provides 5.4 g. of 1,8-octamethylene diisocyanate, b.p. 152°–4°/11 mm. (lit., 146°–8°/mm.); $n_D^{26}$, 1.4528.

Anal., Calc'd for $C_{10}H_{16}N_2O_2$: C, 61.20%; H, 8.22%; N, 14.28%. Found: C, 61.12%; H, 8.31%; N, 14.17%.

Titration of —NCO functionality shows an equivalent weight of 98.7 (calc'd. 98.2).

EXAMPLE 3

To 9.8 g. (2.0 mmoles-OH functionality) of an aqueous dispersion of a 95/5 mole percent ethyl acrylate/hydroxyethyl methacrylate emulsion copolymer (43.6% solids) is added 0.4 g. 0.8 g. (1.0 to 2.0 mmoles) of sebacyl bis(N,N,N-trimethylhydrazonium chloride). The pH is adjusted to 9.0–10.5 by the addition of dilute sodium hydroxide; this provides the free sebacyl N—N ylid. A cast film (initially 10 mils) of the dispersion when baked at 150° for thirty minutes shows substantial crosslinking as determined through solvent swelling measurements. In this test, p-xylene is used as the swelling solvent, the swell ratio is T+ΔT/T where T is film thickness and "dis." means "dissolved".

| Mole Ratio (ylid/resin) | pH | Small Ratio | | |
|---|---|---|---|---|
| | | Air Dried | 150° C./5 min | 150° C./30 min. |
| 0.5 | 9.0 | dis. | dis. | 3.56 |
| 0.5 | 10.5 | dis. | dis. | 3.34 |
| 1.0 | 9.0 | dis. | dis. | 2.92 |
| 1.0 | 10.5 | dis. | dis. | 2.64 |

In the absence of the isocyanate precursor no crosslinking is observed under the same conditions as is evidenced by the complete dissolution of the film on exposure to the swelling solvent.

EXAMPLE 4 bis(N,N-dimethyl hydrazide) of adipic acid

Into a 1 l. three-necked flask equipped with a mechanical stirrer, a nitrogen inlet tube (extending into the solution), and a Y-tube adapter fitted with a reflux condenser and a thermometer extended into the solution, is placed 500 ml. of benzene, 193 g. (2.0 mole) of unsym-dimethylhydrazonium chloride and 183 g. (1.0 mole) of adipyl chloride. A slow sweep of nitrogen is begun and the effluent gas is led from the top of the condenser into a gas scrubber containing water and a small pool of mercury to prevent back-up. The solution is heated to reflux and shortly thereafter, the formation of solid is observed. During the course of the reaction it is necessary to add approx. 300 ml. of benzene to facilitate stirring. At the end of four hours 95% of the calculated amount of hydrogen chloride is obtained. The reaction mixture is allowed to cool to room temperature followed by filtration with suction. The resulting yellow solid, adipyl bis(N,N-dimethylhydrazonium chloride), is washed with a small amount of benzene and dried under reduced pressure, m.p. 202°–205° (decomposition). Titration with aqueous sodium hydroxide shows an equivalent weight of 155.0 (calc'd., 151.6).

To a mixture of 272.5 g. (0.9 mole) of the above solid and 900 ml. of anhydrous methanol is added slowly, with stirring, 389 g. (1.9 moles) of sodium methoxide (25% in methanol). The reaction temperature is maintained below 50° C by periodic cooling with an ice-bath. After the addition, the reaction mixture is stirred for one hour, then filtered. The filtrate is stripped to dryness under reduced pressure and the resulting solid recrystallized from ethanol. The yield of bis(N,N-dimethyl hydrazide) of adipic acid, m.p. 158°–161° is 90.5 g. (43.7% based on the amount of chloride salt employed). An additional 80 g. (38.6%) of product, m.p. 157°–160°, is obtained by concentrating the filtrate followed by subsequent cooling and filtration.

Anal., Calc'd for $C_{10}H_{22}O_2N_4$: C, 52.15%; H, 9.63%; N, 24.33%. Found: C, 51.52%; H, 9.40%; N, 23.99%.

Adipyl bis(N,N,N-trimethylhydrazonium chloride)

A mixture of 69.0 g. (0.30 mole of bis(N,N-dimethyl hydrazide) of adipic acid and 65 g. (1.3 moles) of methyl chloride in 250 ml. of methanol are allowed to react employing the procedure used in Example 1. The reaction mixture is stripped under reduced pressure and the resulting solid recrystallized from ethanol. The yield of adipyl bis(N,N,N-trimethylhydrazonium chloride) is 72 g. (72.5% yield based on the hydrazide).

N,N'-bis(trimethylamino) adipyldiimide

To a mixture of 66.2 g. (0.20 mole) of adipyl bis(N,N,N-trimethylhydrazonium chloride) and 300 ml. of methanol is added with stirring 86.4 g. (0.40 mole) of sodium methoxide (25% in methanol). The reaction mixture is stirred for one hour after which it is stripped to dryness under reduced pressure. The resulting solid is extracted twice with 200 ml. portions of methylene chloride. The combined extracts are stripped under reduced pressure and the solid residue is recrystallized from methanol-ether. The yield of N,N'-bis(trimethylamino) adipyldiimide is 40.3 g. (78.2% based on the hydrazonium salt).

Anal., Calc'd for $C_{12}H_{26}N_4O_2$: C, 55.78%; H, 10.14%; N, 21.69% Found: C, 55.32%; H, 10.54%; N, 21.52%.

EXAMPLE 5

To 9.2 g. (10 mmoles -OH) of low molecular weight polyester prepared from adipic acid, diethylene glycol and trimethylolethane and having an acid number of 2.4, a hydroxyl number of 61 and a viscosity of O+ (75% solids in xylene) is blended 3.14 g. (10 mmoles) of N,N'-bis(trimethylamino) sebacyldiimide. A five mil film of this blend cast on cold rolled steel and baked at 150° for 45 minutes exhibits excellent flexibility, good adhesion, moderate hardness and good resistance to 2-ethoxyethyl acetate for 30 minutes.

When an —NCO/—OH ratio of less than that employed above (2/1) is employed, or when lower temperatures or shorter curing times are used, the solvent resistance (2-ethoxyethyl acetate) decreases.

What is claimed is:

1. A compound of the formula

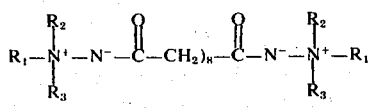

wherein $R_1$, $R_2$ and $R_3$ are each methyl.

* * * * *

UNITED STATES PATENT AND TRADEMARK OFFICE
CERTIFICATE OF CORRECTION

PATENT NO. : 3,989,752
DATED : November 2, 1976
INVENTOR(S) : William D. Emmons

It is certified that error appears in the above-identified patent and that said Letters Patent are hereby corrected as shown below:

In Column 5, line 22, after "8°/", and before "mm.", insert -- 11 --.

In Column 5, line 33, between "0.4 g." and "0.8 g.", insert a dash (-).

In Column 8, Claim 1, correct the formula to read as follows:

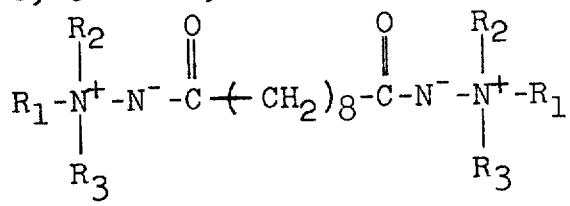

Signed and Sealed this

Twenty-second Day of February 1977

[SEAL]

Attest:

RUTH C. MASON
*Attesting Officer*

C. MARSHALL DANN
*Commissioner of Patents and Trademarks*